United States Patent
Chabrol et al.

(10) Patent No.: US 10,702,697 B2
(45) Date of Patent: Jul. 7, 2020

(54) DEVICE FOR DEEP ELECTRICAL AND OPTICAL BRAIN STIMULATION

(71) Applicant: COMMISSARIAT A L'ENERGIE ATOMIQUE ET AUX ENERGIES ALTERNATIVES, Paris (FR)

(72) Inventors: Claude Chabrol, Poisat (FR); Alim-Louis Benabid, Meylan (FR)

(73) Assignee: COMMISSARIAT A L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 221 days.

(21) Appl. No.: 15/575,191

(22) PCT Filed: May 12, 2016

(86) PCT No.: PCT/FR2016/051124
§ 371 (c)(1),
(2) Date: Feb. 26, 2018

(87) PCT Pub. No.: WO2016/189216
PCT Pub. Date: Dec. 1, 2016

(65) Prior Publication Data
US 2018/0154152 A1    Jun. 7, 2018

(30) Foreign Application Priority Data
May 28, 2015 (FR) ...................... 15 54789

(51) Int. Cl.
*A61N 1/36* (2006.01)
*A61N 1/05* (2006.01)
(Continued)

(52) U.S. Cl.
CPC ....... *A61N 1/36067* (2013.01); *A61N 1/0534* (2013.01); *A61N 1/36082* (2013.01);
(Continued)

(58) Field of Classification Search
USPC .......................................................... 607/45
See application file for complete search history.

(56) References Cited

U.S. PATENT DOCUMENTS

| | | |
|---|---|---|
| 2005/0070987 A1 | 3/2005 | Erickson |
| 2010/0241100 A1* | 9/2010 | Blumenfeld ......... A61B 5/0075 604/503 |
| 2014/0074182 A1 | 3/2014 | Wolf, II |

FOREIGN PATENT DOCUMENTS

WO    WO-2009/026382 A1    2/2009

OTHER PUBLICATIONS

International Search Report issued in Application No. PCT/FR2016/051124 dated Jul. 19, 2016.
(Continued)

*Primary Examiner* — Nicole F Lavert
(74) *Attorney, Agent, or Firm* — Marshall, Gerstein & Borun LLP (57) ABSTRACT

A deep brain stimulation device includes a probe having a transparent distal portion, crossed by a channel open at a proximal end of the probe, and also includes electrodes affixed to the distal portion of the probe and electrode terminals affixed to a proximal portion of the probe. Further, the device includes an electrical housing including a channel open at its two ends and housing electrical terminals in contact with the terminals of the probe, and an electrical extension lead affixed to the housing and connected to the terminals of the housing. The channel of the housing is open at the other one of its ends and the device further includes a waveguide at least partly housed in the central channel of the probe, all the way to the distal portion of the probe, and a transmitter housing capable of being connected to the waveguide for the injection of a predetermined wavelength.

6 Claims, 6 Drawing Sheets

(51) Int. Cl.
*A61N 5/06* (2006.01)
*A61N 5/067* (2006.01)
*A61B 5/04* (2006.01)
*A61B 5/00* (2006.01)

(52) U.S. Cl.
CPC ......... *A61N 5/0601* (2013.01); *A61N 5/0622* (2013.01); *A61B 5/04001* (2013.01); *A61B 5/4836* (2013.01); *A61N 1/3606* (2013.01); *A61N 2005/063* (2013.01); *A61N 2005/067* (2013.01); *A61N 2005/0612* (2013.01); *A61N 2005/0628* (2013.01); *A61N 2005/0632* (2013.01); *A61N 2005/0651* (2013.01); *A61N 2005/0653* (2013.01); *A61N 2005/0659* (2013.01); *A61N 2005/0662* (2013.01)

(56) References Cited

OTHER PUBLICATIONS

Rubehn, B. et al., "Polymer-Based Shaft Microelectrodes with Optical and Fluidic Capabilities as a Tool for Optogenetics," *Engineering in Medicine and Biology Society, EMBC, 2011 Annual International Conference of the IEEE* (Aug. 30, 2011).

Pitzschke, A. et al., "Red and NIR light dosimetry in the human deep brain," *Physics in Medicine and Biology* (2015).

Reinhart, F. et al., abstract of "High Resolution MR-thermometry is a proper method to characterize thermal safety of chronic implantable medical device," Society for Neuroscience Annual Meeting (Nov. 2014).

* cited by examiner

DEVICE FOR DEEP ELECTRICAL AND OPTICAL BRAIN STIMULATION

TECHNOLOGICAL FIELD

The present disclosure relates to the field of devices implantable in a human or animal brain, and more particularly to the field of devices performing deep brain simulation, particularly for the treatment of neurodegenerative diseases such as Parkinson's disease.

BACKGROUND

Deep brain simulation (DBS) comprises electrically stimulating with low-current pulses portions of the human brain controlling the movements, and more particularly the thalamus, the Luys nucleus, and/or the globus pallidus, which enables the patient to better control his/her movements. Such a stimulation is successfully used to treat Parkinson's disease, tremor, OCDs or dystoniae.

Figure 1:
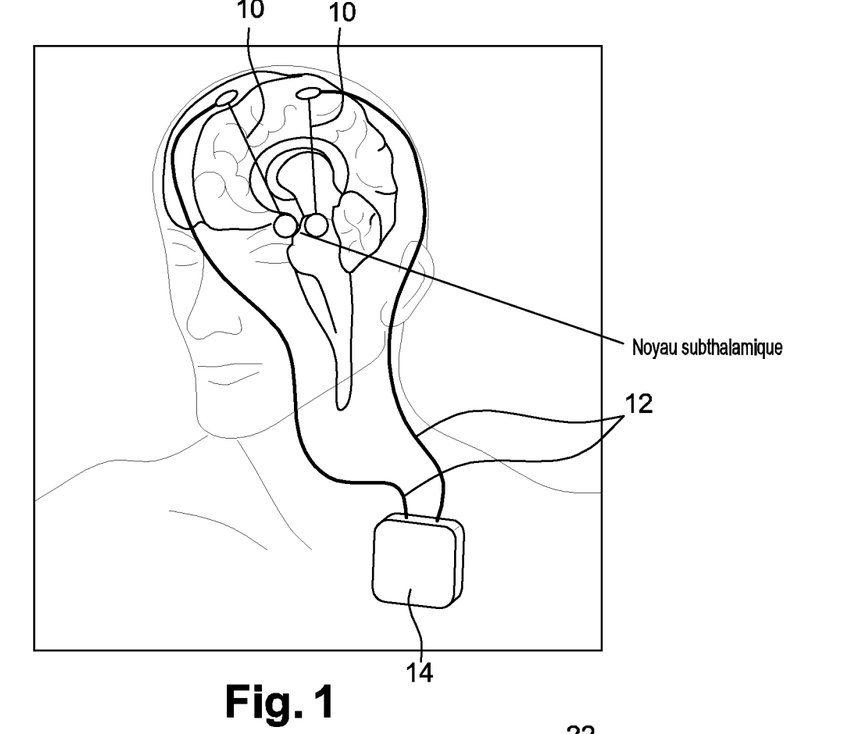
FIG. 1 is a simplified view of a probe, of connectors, and of stimulators for the deep electrical stimulation of a human brain.

In practice, referring to FIG. 1, two sets of electrodes 10 are implanted in the brain for the electric stimulation thereof, each of these sets being arranged at the end of a flexible longilineal body made of a biocompatible material, also called "DBS" probes. The implantation of a probe comprises forming an opening in the patient's skull cap to introduce the probe through the trepanation to place its distal end at the desired location, using for this purpose real time brain imaging (scanner, MRI . . . ) and three-dimensional brain reconstruction. Due to the material forming it and/or to its diameter, the probe is usually highly flexible and difficult to introduce into the brain by simple pushing. Thereby, the probe is provided with a central channel into which the practitioner introduces a rod of low flexibility, called "stiffener", which helps, or even simply makes possible, the progress of the probe into the brain by pushing.

During this operation, the patient is under local anesthesia so that tests can be performed as to the efficiency of the simulation. Once the probes are in place, the patient is then put under general anesthesia, and an extension 12 of each probe is arranged under the scalp and the neck skin for the connection of the probes to an electric cell stimulator 14 arranged under the patient's skin in subclavicular position.

In the following, term "distal" relates to a portion or an end of an element, intended to be in contact with the area to be treated. Term "proximal" relates to a portion or an end of the element, opposite to the distal portion or end and usually intended for the connection of the element to a stimulator.

Many DBS probes have thus been designed, for example, by Medscape©, Medtronics©, BostonScientic©, etc. . . . .

Figure 2:
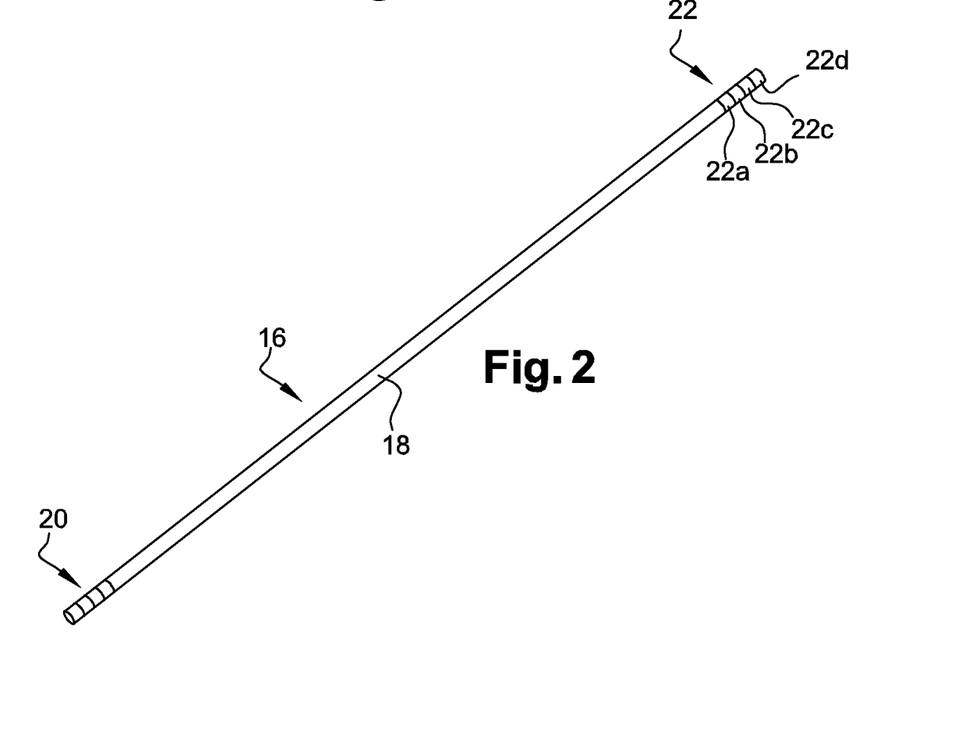
FIG. 2 is a simplified perspective view of a DBS probe of the state of the art.
Figure 3:
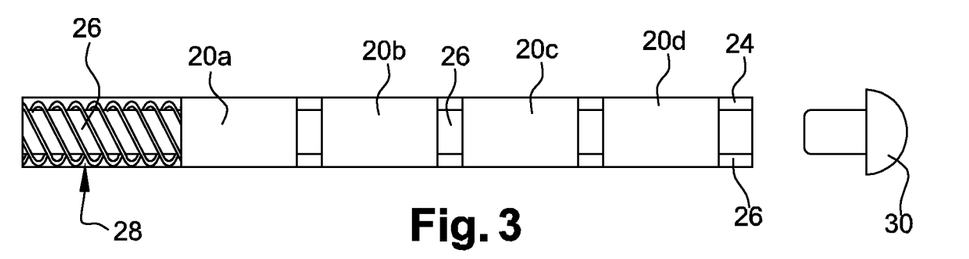
FIG. 3 is a simplified view of a distal portion of the DBS probe of FIG. 1.
Figure 4:
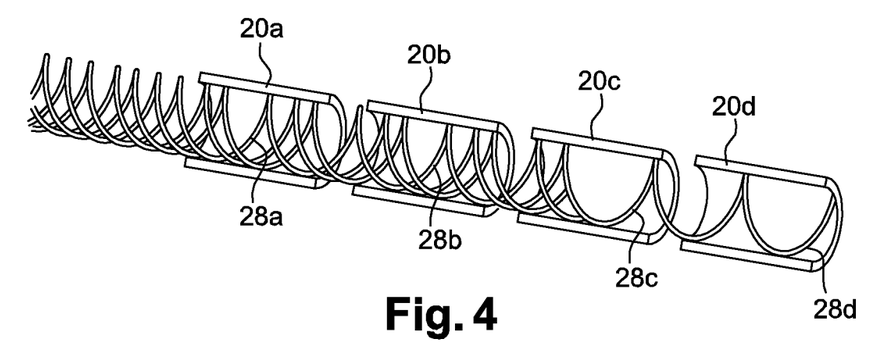
FIG. 4 is a simplified view of the electrical stimulation electrodes of the DBS probe and of the conductive wires supplying the electrodes.

Referring to FIGS. 2 to 4, a DBS probe 16 usually comprises:

a flexible electrically-insulating cylindrical longilineal probe body 18, of small diameter, typically 1.3 mm, where the probe body may be a simple tube (MEDTRONIC) or a multi-lumen tube (Boston Scientific);

an assembly 20 of electric stimulation electrodes 20a, 20b, 20c, 20d arranged in a distal portion of body 18, and an assembly 22 of power supply contacts 22a, 22b, 22c, 22d arranged in a proximal portion of body 18.

Electrodes 20a, 20b, 20c, 20d, often four, take the shape of electrically-conductive cylinders surrounding an outer surface of probe body 18. The latter further comprises at its center a hollow tube 26, void of material, which extends all along the length of body 18, and having a diameter usually from 0.45 to 0.55 mm to allow the introduction during the surgery of a metallic stiffener having a diameter from 0.3 to 0.35 mm.

An assembly 28 of electrically-insulated conductive wires 28a, 28b, 28c, 28d is wound around tube 26, respectively welded to electrodes 20a, 20b, 20c, 20d and to contacts 22a, 22b, 22c, 22d, and embedded in the material of probe body 18. Wires 28a, 28b, 28c, 28d typically have a diameter in the range from 100 µm to 150 µm.

The distal end of probe body 18 is further closed by a hemispherical plug 30 inserted into hollow tube 26. Thus, the central channel is tightly closed (except at the proximal end of the probe), to avoid any introduction of fluid into it, but also to avoid a contamination of the brain via the central channel during the implantation of the probe. Contacts 22a, 22b, 22c, 22d are generally also cylinders enclosing an outer proximal surface of probe body 18, and respectively connected to conductive wires 28a, 28b, 28c, 28d, with a dimension and spacing which may however be different from those of electrodes 20a, 20b, 20c, 20d.

Figure 5:
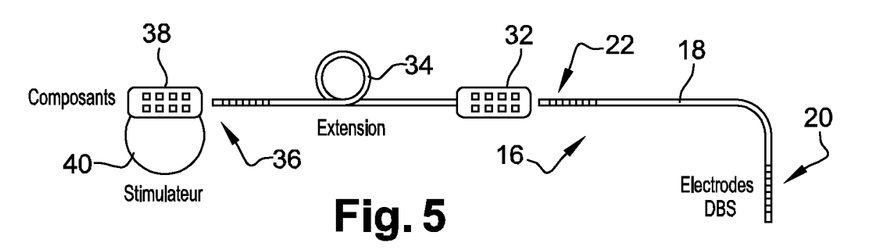
FIGS. 5 and 6 are simplified views of the different components used for the deep electric stimulation, respectively before their connection and after their connection.
Figure 6:
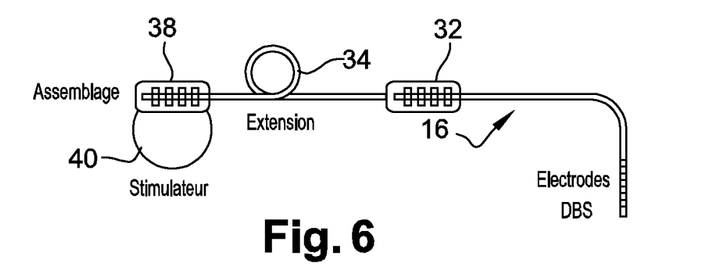

Referring to FIGS. 5 and 6, the electric connection of a DBS probe 16 comprises introducing the proximal portion thereof, provided with contacts 22a, 22b, 22c, 22d, into the channel of an electrical housing 32, comprising inner contacts/terminals which respectively come into contact with contacts of the probe 22a, 22b, 22c, 22d. Housing 32, which forms a simple electrical contacting area and thus comprises no electric control element, extends in an extension lead 34, provided with contacts 36 in a proximal portion for a connection to connectors 38 of an electric stimulator 40.

In parallel with deep electrical brain stimulation, deep optical brain stimulation arouses an increasing interest, particularly optical stimulation by means of a radiation in visible red or near infrared, for the treatment of the same diseases as those treated by the electric stimulation, as for example described in article "*Red and NIR light dosimetry in the human deep brain*" of A Pitzschke et al., *Phys. Med. Biol.* 60 2921, 2015. This new approach particularly induces the development of new probes provided, in distal position, with optical outlets, generally based on specific polymer materials which should have both the desired optical emission and biocompatibility properties.

The electrical stimulation only compensates for the lack of dopamine by exciting the Luys nucleus, but has no therapeutic effect on Parkinson's disease, which keeps on evolving. The results observed on preclinical tests show that an optical stimulation provides a cellular protection of the cells of the SNc, which cause Parkinson's disease as they degenerate. The combination of the two stimulation modes would provide a cellular protection and thus stop the disease, while decreasing the symptoms (akinesia, stiffness, tremor . . . ) by stimulating the Luys nucleus in patients already in an advanced phase of the disease. It is thus not excluded to combine the two approaches to stimulate a same area of the brain to treat a specific disease, for example, Parkinson's disease. This however implies multiplying the number of probes implanted in the brain, which is hardly conceivable. As a variation, it is possible to design probes which each comprise two sets of electrodes in distal position, one set of electrodes for electric stimulation and one set of electrodes for optical stimulation. This however implies a rather large optoelectrical emission area of the probe, and thus possible a treatment which has too low a spatial selectivity, in addition to the multiplication of the conductive wires to be provided in the probe. It is also possible to attempt designing electrodes which are adapted to both stimulation types, electrical and optical, and which are further biocompatible. The difficulty implied by the development of such electrodes can thus easily be conceived.

SUMMARY OF THE DISCLOSURE

The described embodiments aim at providing a deep optoelectrical brain simulation device which has a simple design.

To achieve this, the described embodiments aim at a deep brain stimulation device comprising:
a stimulation probe comprising:
a longilineal body having a central channel void of material running therethrough, extending between a distal portion and a proximal end of the probe, the central channel being open at said proximal end and the distal portion of the body being capable of transmitting a predetermined wavelength;
electrodes affixed on an outer surface of the body in the distal portion of the probe for the electric brain stimulation;
electrical terminals each comprising a portion affixed to an outer surface of the body in the proximal end of the probe and connected to the electrodes for their electric power supply;
an electrical housing comprising a channel having electrical terminals housed therein, said channel being open at one of its ends to receive the proximal portion of the probe in order to place into contact the electrical terminals of the probe and the electrical terminals of the housing; and
an electrical extension lead affixed to the electrical housing and connected to the electrical terminals of the housing.
According to embodiments:
the channel of the electrical housing is open at the other one of its ends;
and the device further comprises:
a waveguide capable of guiding the predetermined wavelength, housed at least partly in the central channel of the probe body, and extending all the way to the distal portion of the probe for the illumination of the brain therethrough; and
a transmitter housing capable of being connected to a proximal end of the waveguide for the injection into it of the predetermined wavelength.

In other words, various embodiments are described based on the observation by the inventors of the fact that DBS probes of the state of the art may be simply modified to also implement an optical stimulation. Indeed, a DBS probe has a central channel which is not used for electric stimulation, the material of the probe body (e.g., silicone, or polyurethane) is usually transparent to wavelengths of interest for the optical stimulation, and the electrical stimulation electrodes do not cover the entire distal portion of the probe, particularly the end thereof, which thus leaves a surface area for optical emission. Further, the diameter of the channel of probes of the state of the art is compatible with the diameter of certain optical fibers capable of transporting the wavelength for the optical stimulation.

Thus, by introducing an optical fiber into the central channel of a DBS probe all the way to the distal end thereof, a modified probe which, on its distal portion, is capable of emitting electrical stimulations by means of the electrodes and an optical emission at least through the distal end of the probe, is obtained. Further, in case of need, the fiber, which is removably housed in the central channel, may be removed or repositioned. Advantageously, the waveguide is introduced once the probe has been implanted, thus signifying that the central channel keeps its original function, that is, the reception of a stiffener helping the progress of the probe in the brain.

However, the electric connection of a DBS probe of the state of the art is invariably performed by means of an extension lead which obstructs the central channel, so that, as such, it is not possible to introduce a waveguide (e.g., an optical fiber) into the probe channel and to connect this waveguide.

According to the described embodiments, the connectors of the DBS probe are thus modified to avoid obstructing the channel of the electrical housing by offsetting the electrical extension lead affixed to the housing. The housing channel being unobstructed, the waveguide can thus be introduced into it and the connection of the waveguide to a light emission source can be allowed.

According to embodiments, the device comprises one or a plurality of the following features:
the distal portion of the waveguide and the distal portion of the probe have a width in the range from 2 millimeters to 10 millimeters;
the wavelength is in the range from 670 nanometers to 1,070 nanometers, and preferably from 670 to 810 nanometers, and the optical power transmitted by the distal portion of the waveguide is smaller than or equal to 10 milliwatts, particularly for the treatment of Parkinson's disease;
the waveguide is a HCS-type optical fiber ("hard-clad silica") having a silica core with a diameter in the range from 125 micrometers to 300 micrometers, a coating (or "cladding") having a diameter smaller than or equal to 15 micrometers and a cladding (or "buffer") having a diameter smaller than or equal to 500 micrometers, or any other waveguide (silicone, PMMA, Silica-silica) having a diameter smaller than or equal to 500 micrometers.

The present embodiments also aim at an electrical extension for a connection with a deep brain stimulation probe, said probe comprising a longilineal body and electrical terminals affixed to an outer surface of a proximal portion of the probe body, said electrical extension comprising:
an electrical housing comprising:
a channel open at a first and a second ends, the channel being capable of receiving the proximal portion of the body of the probe when the latter is introduced through the first end of the channel;
electrical contacts housed in the channel of the electrical housing and capable of coming into contact with the terminals of the probe when the proximal portion thereof is introduced into the housing channel through the first end of the channel;
and an electrical extension lead comprising electrical conductors connected to the electrical contacts of the housing, said electrical extension lead being affixed to the housing without obstructing the second end of the channel of the housing.

Such an extension enables to connect a DBS probe by leaving its central channel unobstructed. Advantageously, this extension is universal since it can supply a DBS probe, be it associated or not with a waveguide.

Advantageously, a plug, e.g. made of silicone, is used to obstruct the central channel if the latter is not used to house a waveguide. The plug may be a septum molded at the same time as the body of the connector or a part which snaps thereto.

The disclosed embodiments also aim at a method of testing the optical operation of a first and a second stimulation devices of the previously-described type, the probes of the two devices being pre-implanted in the brain with their distal portions housed in an area of the brain to be treated, the method comprising:

injecting a radiation having a predetermined wavelength into the waveguide of the first device through the proximal end of the waveguide and measuring said radiation at the proximal end of the waveguide of the second device;

injecting the same radiation into the waveguide of the second device through the proximal end of the waveguide and measuring said radiation at the proximal end of the waveguide of the first device; and diagnosing the optical operation of the assembly formed by the probes and the waveguides housed therein according to the measurements.

As previously described, DBS probes of the state of the art may be simply modified to also implement an optical stimulation, including DBS probes which are already implanted in a patient. It is thus possible to update already-implanted probes, without having to remove them, by introducing waveguides (e.g. optical fibers) into their respective central channel, while providing the new connectors according to the contemplated embodiments. It should however be made sure that the optical fibers have effectively been introduced and that the optical operation of the modified probes meets the expectations. Now, by nature, a waveguide is also capable of capturing a radiation with its ends. Thus, when the optical emission of the first probe (respectively of the second probe) is activated and the emission of the second probe (respectively of the first probe) is deactivated, said second (or first) probe thus captures with its distal end the radiation of the first probe (respectively of the second probe), the optical radiation thus collected propagating to the proximal end of the probe where it is measured in order to be analyzed. The optical operation of the probes can thus be diagnosed with the DBS probes still implanted.

BRIEF DESCRIPTION OF THE DRAWINGS

The embodiments described herein will be better understood on reading of the following description provided as an example only in relation with the accompanying drawings, where.

DETAILED DESCRIPTION

Figures 7A, 7B:
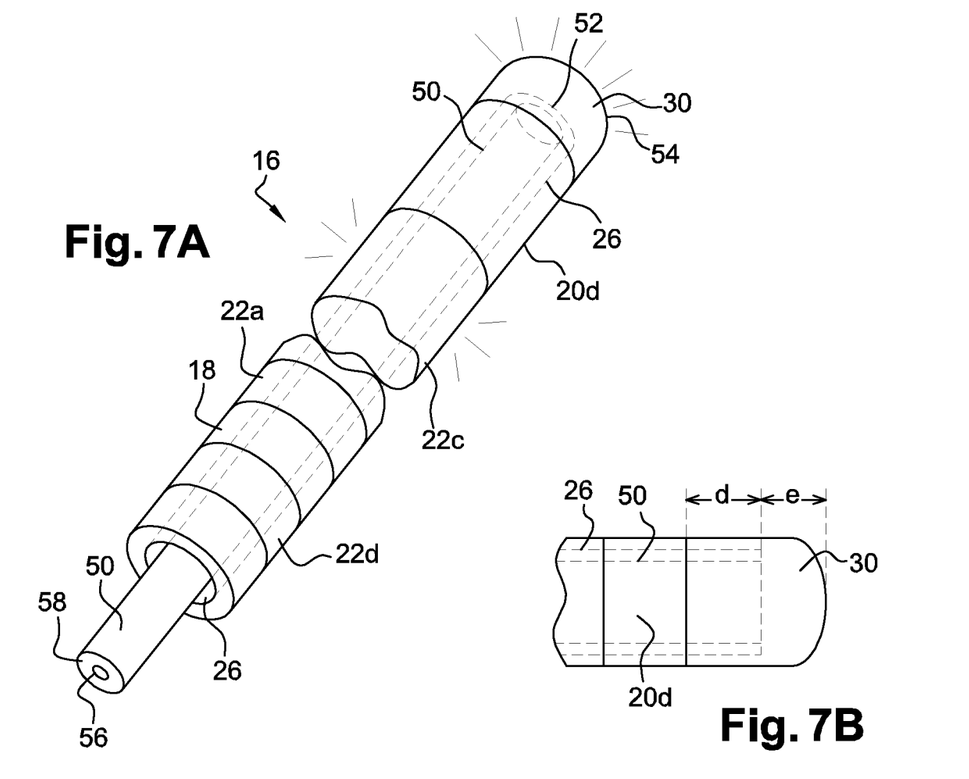
FIG. 7A is a simplified perspective view of a DBS probe having an optical fiber inserted into it and FIG. 7B is an enlarged view of the distal portion of the DBS probe of FIG. 7A.

Referring to FIGS. 7A and 7B, a DBS probe 16, for example, that described in relation with FIGS. 2 to 4, comprises a body 18 and a hemispherical cap 30 made of a material transparent to a radiation of interest, that is, giving way to at least 95% of the radiation, for example, transparent to a red or near infrared wavelength. For example, body 18 is made of polyurethane, of silicone, or of epoxy which has a high red or near infrared optical transmission rate while having a refraction index (of 1.43 for silicone, for example) close to that of the cerebrospinal fluid (equal to 1.38).

Probe 16 is further associated with an optical fiber 50 removably introduced into and all the way to the end of tight central channel 28 of the probe, the end of optical fiber 50, advantageously previously cleaved, also being in contact with the end of the central channel. Fiber 50 can thus transmit the electromagnetic radiation at the level of the portion of probe 16 intended for electrical brain stimulation, and particularly at least across plug 30.

Particularly in the context of the treatment of Parkinson's disease, and as illustrated in FIG. 7B, central channel 28 extends beyond the last electrical stimulation electrode 20d across a distance d sufficient for the distal end of the channel, and thus for plug 30 having the illumination performed therethrough, to be positioned in the patient's SNc while electrode 20d is positioned in the patient's Luys nucleus. Particularly, distance d is for this purpose in the range from 15 mm to 20 mm.

Advantageously, light-emitting length e of plug 30 is in the range from 2 to 5 mm to locally illuminate the SNc portion of the substantia nigra. A length of a few mm of the light diffusion enables to improve the uniformity of the illumination of a large surface area.

Optical fiber 50 is for example a multimode HCS ("hard-clad silica") fiber having a core 56 with a diameter smaller than 500 micrometers, for example, in the range from 125 to 300 micrometers, coated with a cladding 58, for example, an optical fiber of reference K200/230 Polymer Cladded Fiber of LEONI FIBER OPTICS. Such fibers have the advantage of being biocompatible and further allow a high-quality optical guiding, even when they are curved.

Advantageously, the optical fiber may undergo a mechanical treatment, for example, cladding 58 may be treated by sandblasting, on a distal portion or a portion located along the fiber, to form holes exposing its core 56, which enables to increase the fiber emission surface area, or to locally decouple part of the light and particularly enable a determined percentage of the light flow to be transmitted between the spaces between electrodes of probe 16. Other solutions such as the laser marking of µ structures inside of the fibers provide the same effect of local extraction of a percentage of the light power.

Figure 8:
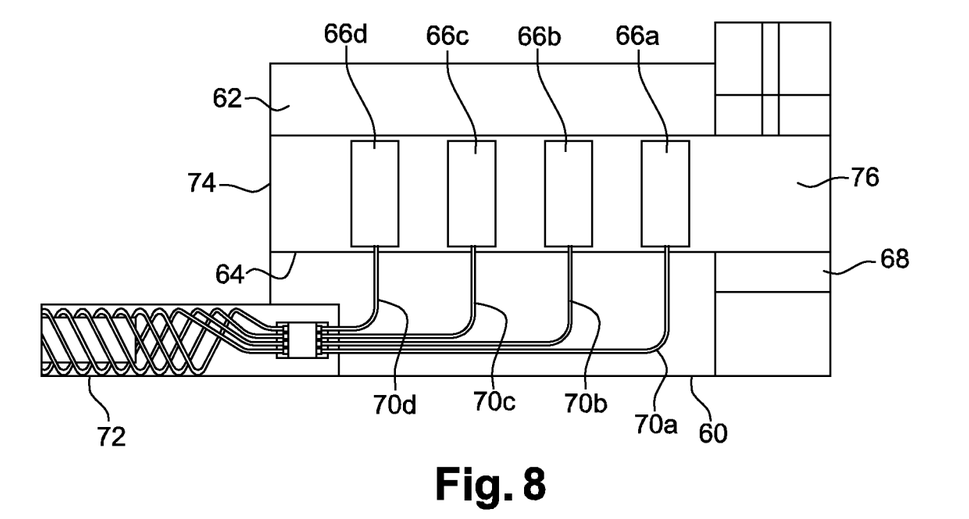
FIG. 8 is a simplified view of an electrical connection housing for the connection to the proximal portion of a DBS probe provided with electrical contacts.

For the electric connection of contacts 22a, 22b, 22c, 22d, an electrical housing 60, such as illustrated in FIG. 8, is provided. Housing 60 comprises an electrically-insulating body 62 made of a biocompatible material, thoroughly crossed by a cylindrical channel 64 having a diameter slightly smaller than the diameter of the proximal portion of probe 16. Channel 64 comprises cylindrical electrical contacts 66a, 66b, 66c, 66d defining for example an inner surface of channel 64, and having their dimensions and spacing corresponding to the dimensions and spacing of contacts 22a, 22b, 22c, 22d. Thus, when the proximal portion of probe 16 is introduced into channel 64, the contacts of the probe and of the channel respectively come into contact, the probe being then locked in position by a locking part 68 of housing 60. The elements which have just been described for example correspond to extension model 37083 manufactured by Medtronics. Housing 60 has a contacting function and comprises no control element (microprocessor, battery, etc.), these elements being contained in stimulator 40.

Advantageously, conductive wires 70a, 70b, 70c, 70d are respectively connected to contacts 66a, 66b, 66c, 66d and housed across the thickness of body 62. This enables to form an electrical extension lead 72, which is affixed to housing 60 without obstructing opening 74 of channel 64, opposite to opening 76 through which the DBS probe is inserted. Housing 60 and extension lead 72 thus form an electrical extension for the connection of the DBS probe to a stimulator, which enables to insert the optical fiber into the central channel of the DBS probe and to connect it to optical connectors.

Figure 9:
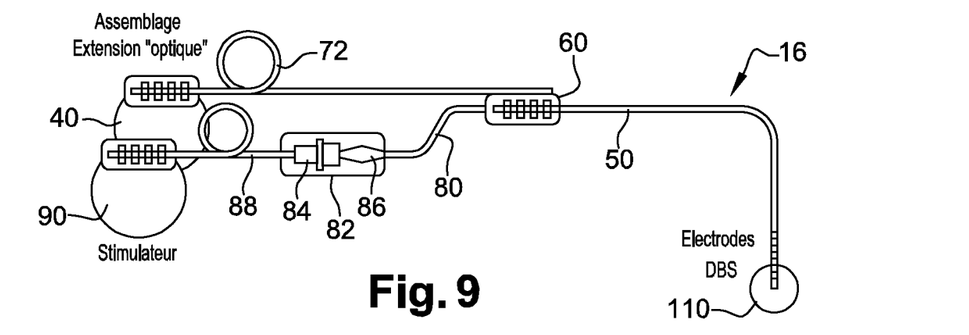
FIG. 9 is a simplified view illustrating a deep optoelectrical brain stimulation system.

Referring to FIG. 9, the connection of the DBS probe and of the optical fiber inserted into it comprises:

for deep electrical stimulation, electrical extension 60, 72 connected to an electrical stimulator 40;

for deep optical stimulation, an optical extension forming a waveguide 80 axially continuing optical fiber 50 in the channel of electric connection housing 60, a transmitter housing 82 having extension 80 connected thereto and comprising an emission source 84 capable of injecting into extension 80 radiation 86 at the wavelength of interest, particularly at 670 nanometers. For example, emission source 84 comprises a laser diode (for example, a laser diode of reference HL6756MG of Thorlabs Inc.), a LED ("Light-Emitting Diode", for example, a LED bearing reference SMT670 of Epitex), an OLED ("Organic Light-Emitting Diode"), or a VCEL ("vertical-cavity surface-emitting laser"). An electrical extension lead 88 affixed to transmitter housing 80 is also provided for the connection of emission source 84 with an optical stimulator 90, which controls the operation thereof.

Electrical connection lead 80 and optical fiber 50 for example comprise, at their respective connection end, connectors enabling to optically continue the fibers, as known per se in the state of the art. For example, a proximal portion of fiber 50 is glued in a concentric channel machined in a ceramic or steel ferrule having a calibrated diameter (e.g. standard diameters between 1.25 and 2.5 mm) to guarantee a good repeatability of the positioning during the connection in an optical feedthrough (receptacle) for coupling to a laser source.

Advantageously, optical stimulator 90 is a conventional neurostimulator, e.g. a stimulator having a structure identical to that of the stimulator 40 used for electrical stimulation. Indeed, as known per se, this type of stimulator programmably delivers control signals and electric power supply voltages/currents onto terminals having electrical extension lead 72 connected thereto. A stimulator can thus be programmed to send signals on the electrodes alternately with or at the same time as the control of light source 84.

As a variation, a single stimulator is provided to control the electrical and optical stimulation, this stimulator being equipped with connectors for electrical extension lead 72 and connectors for optical extension lead 80.

Optical stimulator 90 especially controls the optical power of the source, to obtain on the distal portion of the DBS probe the desired optical power. More particularly, for a 670-nm wavelength, the power is selected to be lower than 10 mW, which enables to limit the heating of the brain area, as described in document "High Resolution MR-Thermometry is a proper method to characterize thermal safety of chronic implantable medical device", Reinhart, F., et al, Society for Neuroscience Annual Meeting, November 2014.

The elements which have just been described are made of biocompatible materials. For example, the electrically-insulating materials are made of silicone, polyurethane, Kapton®, etc, and the electrically-conductive materials are made of a nickel-cobalt-chromium-molybdenum alloy, particularly the alloy sold under reference "MP35N®" by Carpenter Technology Corp., Pennsylvania, USA.

Advantageously, optical stimulator 90 comprises a circuit of protection against electrostatic discharges or ESD ("electrostatic discharge") circuit, in particular when emission source 84 is a laser diode, a VCSEL, or a microLED, which are sensitive to electric discharges.

Figure 10A:
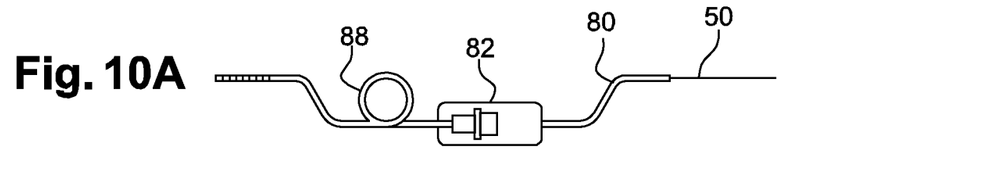
FIGS. 10A and 10B are simplified views illustrating a first and a second variations integrating the connection of an optical extension lead to a transmitter housing forming part of the system of FIG. 9.
Figure 10B:
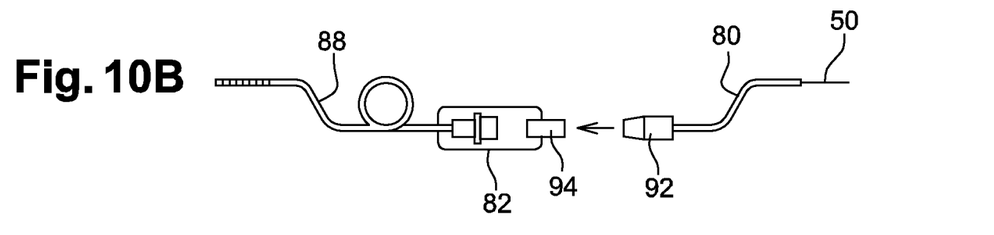

Referring to FIGS. 10A and 10B, according to a first variation (FIG. 10A), extension 80 optically connecting transmitter housing 82 to optical fiber 50 is firmly affixed to housing 82. According to a second variation (FIG. 10B), the extension is removably affixed to housing 82 and for example comprises an end cap 92 which engages in fluidtight fashion with a complementary base 94 of housing 80, which enables to ease the assembly procedure during the surgery and to carry out a test relative to the proper operation/positioning of the optical fiber when it is inserted in the DBS probe, as will be described hereafter.

A method of updating a pair of DBS probes already implanted in a brain, for example, of a human patient, to provide them with the illumination function, is now described in relation with FIGS. 11 to 15.

Figure 11:
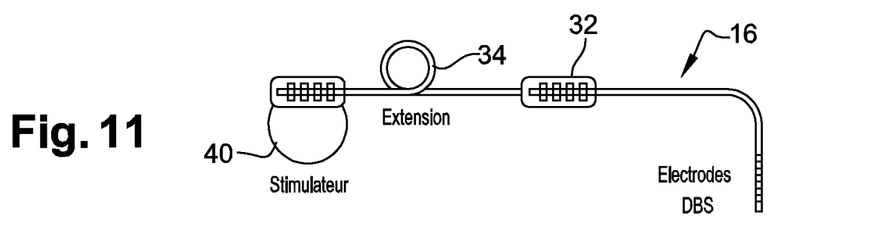
FIGS. 11 to 15 illustrate a method of updating a pair of DBS probes implanted in a patient to give them the optical stimulation function, FIG. 14 more particularly illustrating a method of testing the proper optical operation of the modified probes.
Figure 12:
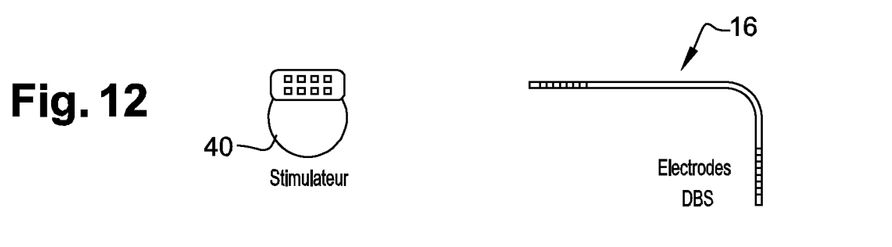
Figure 13:
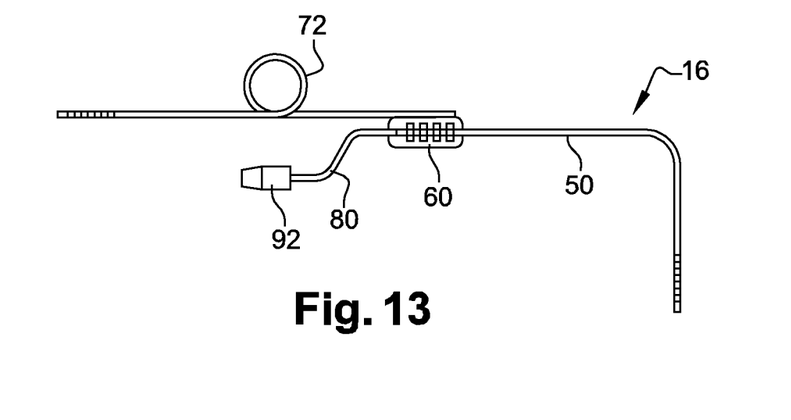

In FIG. 11, a DBS probe 16 is illustrated such as implanted in the patient, and thus connected to electrical extension lead 32, 34, and to stimulator 40. The method thus comprises, in a first step, operating on the patient to be able to remove electrical extension lead 32, 34 and stimulator 40 if the latter is not compatible with the optical update (FIG. 12) while leaving in place DBS probe 16.

At a next step (FIG. 13), the distal portion of the DBS probe is introduced into the central channel of an electrical housing 60 and locked in position. An optical fiber 50 is then inserted into the central channel of DBS probe 16 through the channel of housing 60, until the fiber reaches the distal end of the probe. An optical extension lead 60, advantageously the removable variation described in relation with FIG. 10B, is then connected to optical fiber 50 or is already assembled with optical fiber 50 during its insertion into the central channel of the DBS probe.

Once this operation has been performed for the two implanted DBSs, a method of testing their proper optical operation is then implemented. More particularly (FIG. 14), optical extension leads 80 of the two DBS probes 16 are connected to a first and a second terminals 102, 104 of a test device 100. The latter comprises an emission source 106 enabling to inject the radiation at the treatment wavelength into the optical extension lead connected to first end 102, and an optical detection circuit 108, for example, based on the photodiode, which measures the quantity of radiation received by extension lead 80 connected to second end 104.

Figure 14:
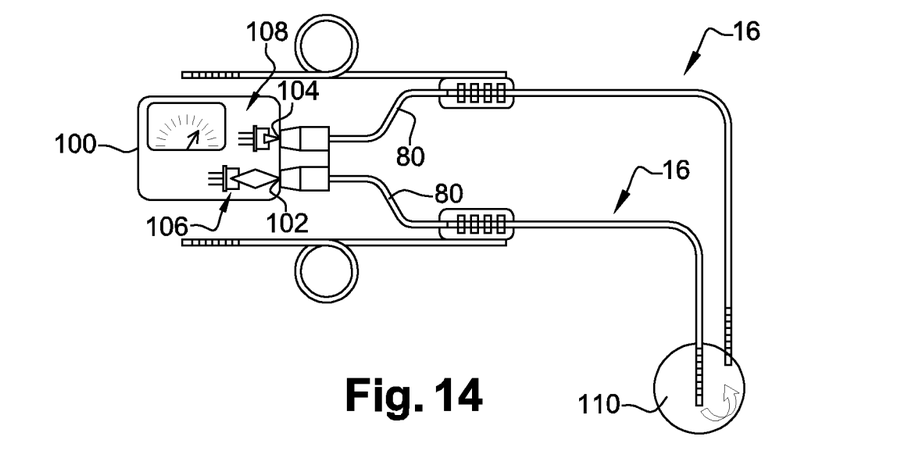
Figure 15:
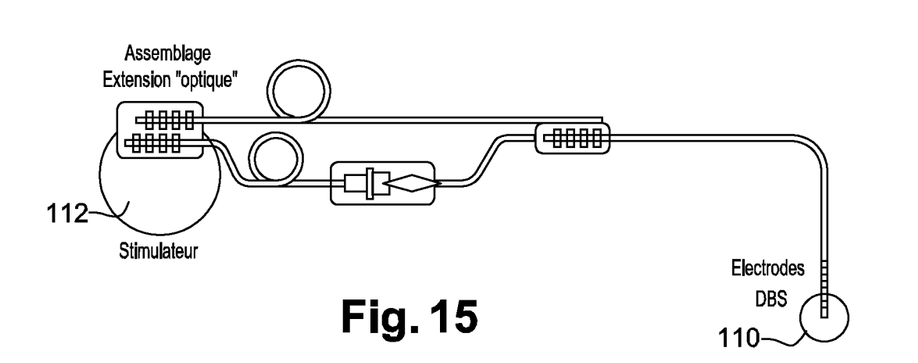

The radiation transmitted by the DBS probe connected to first end 102 thus diffuses through the treated brain area 110 and part of the diffused radiation is collected by the optical fiber inserted into the other DBS probe. The radiation thus collected is transported all the way to the detection circuit of test device 100, where it is measured. Once this measurement has been performed, the connection of extension leads 80 to test device 100 is inverted to perform a second measurement, and then the two obtained measurements are analyzed to determine the proper optical operation of the DBS probes. For example, it is considered that this operation is satisfactory when each of the measurements is higher than a predetermined threshold. Advantageously, this analysis is automatically carried out by optical detection circuit 108 which comprises for this purpose a processing unit based on a microprocessor.

If the proper optical operation of DBS probes is established, the method of updating the latter carries on (FIG. 15) with the replacing of electrical stimulator 40 by a stimulator 112 configured both for optical stimulation and electric stimulation, electric and optical extension leads 72, 80 are connected to stimulator 112, and the latter is started.

Figure 16:
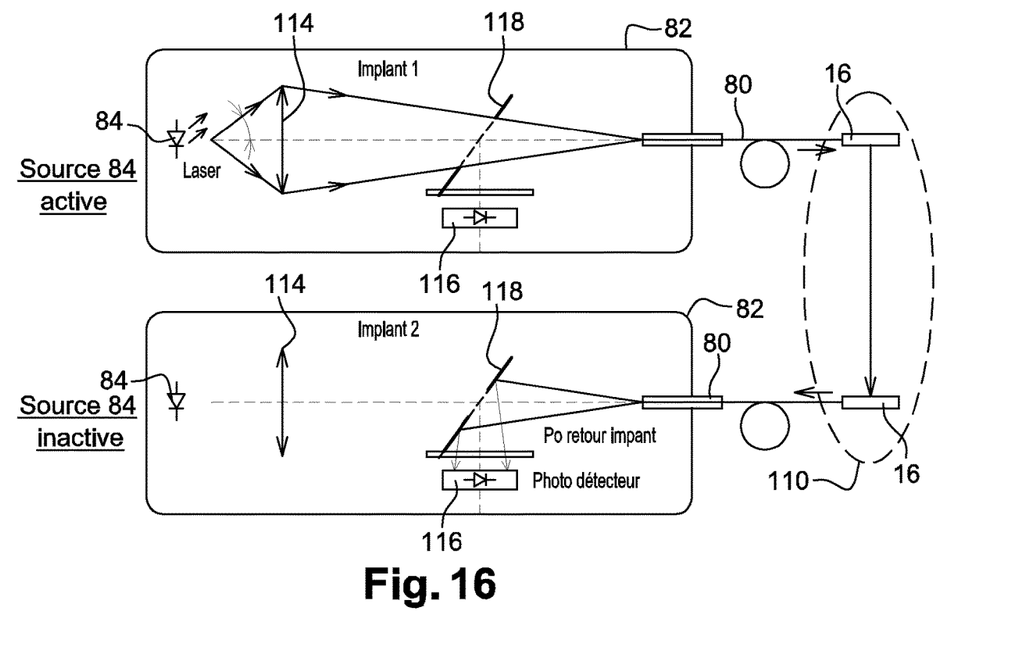
FIG. 16 is a simplified view illustrating a preferred variation of the transmitter housing provided with a radiation detection function.

Referring to FIG. 16, which illustrates in simplified fashion a pair of optoelectrical stimulation probes and their respective transmitter housing 82, the transmitter housing 82 of each of the probes also implements an electromagnetic radiation detection function. Particularly, housing 82 comprises an emitting source 84, an optical system 114 focusing the radiation of source 84 on optical extension lead 80 to inject the radiation into it, a photodetector 116, and a semi-transparent mirror. The mirror gives way to the radiation emitted by source 84, as illustrated in the upper portion of FIG. 16, and deviates part of the radiation originating from extension lead 80 to photodetector 116, as illustrated in the lower portion of FIG. 16. As a variation, the optical fiber has a digital aperture (e.g. equal to 0.37) greater than the angle of injection into the extension lead (e.g. equal to 0.2). The beam transmitted by extension lead 80 is thus wider than the beam focused on extension lead 80. Housing 82 then comprises a mirror 118, for example, ring-shaped, which does not hinder the light beam focused on optical extension lead 80 while being located on the beam transmitted by extension lead 80. The portion of the transmitted beam incident on mirror 118 is then redirected towards photodetector 116.

Photodetector 116 is further connected to stimulator 112 through extension lead 88 connecting housing 82 to stimulator 112. The latter is then configured to treat the measurement delivered by photodetector 116 to determine whether the detected radiation is in accordance with a proper operation.

Figure 17A:
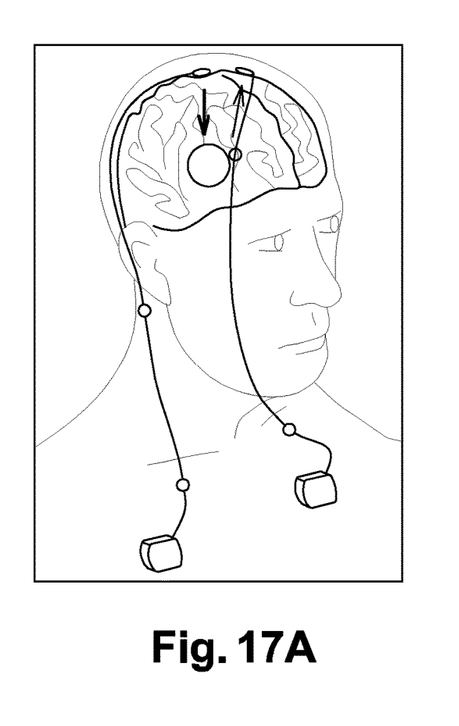
FIGS. 17A and 17B illustrate the alternation of activation and of deactivation of the optoelectrical probe illumination function, enabling to automatically test the operation thereof once the patient has been equipped with systems.
Figure 17B:
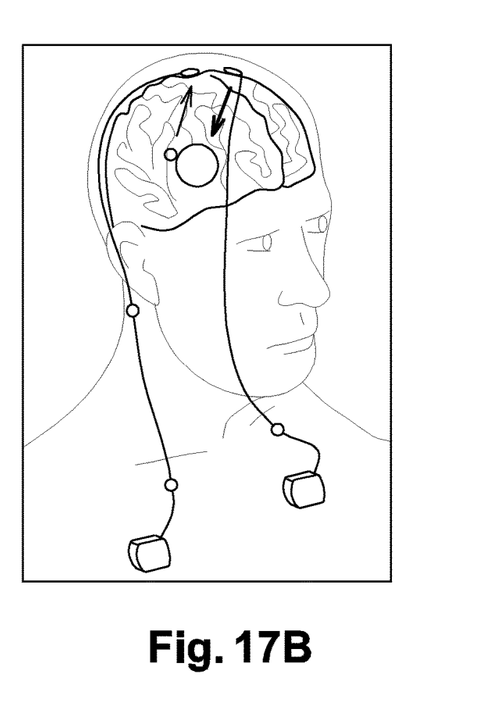

Thus, by deactivating the illumination of a probe, it is possible to test the proper operation of the other probe, similarly to what has been described in relation with FIG. 14, and to do the same for the other probe, as illustrated in FIGS. 18A and 18B. The proper optical operation of the probes may thus be tested at any time on the patient, automatically, and without having to perform any surgery.

Specific embodiments have been described. Multiple variations are of course possible, particularly concerning the connections, extension leads, etc.

Particularly, the following features may be introduced, alone or in combination:

to limit light losses and the risk of breakage of the waveguide (e.g. optical fiber), a "probe stop" imposing a minimum radius of curvature to the probe in its proximal portion placed at the trepanation level;

a tool for protecting the waveguide at the outlet of the optoelectrical base and used for the centering between the fiber and the central channel of the DBS probe during the installation of the device is used;

to ease the insertion of the optical fiber, and particularly the passing of a bend, a hemispherical end is formed, for example, a ball, at the distal end of the fiber by deposition of UV-crosslinkable glue followed by the UV crosslinking. This operation can be carried out by means of a tool compatible with an intervention in a surgical block in the case where the probe length needs to be accurately adjusted by cleaving of the fiber, which leaves a straight end and thus makes the insertion into a channel uneasy. The tool enables to automatically deposit glue and a "secure" crosslinking by electric arc (fiber welding machine);

prior to the insertion of the optical fiber into the DBS probe, liquid silicone, chronically implantable, with a high refraction index, and which decreases losses by reflection at the probe end and limits the risk of infiltration of physiological fluids, is injected into the central channel of the probe.

The invention claimed is:

1. A deep brain stimulation device comprising:
   a stimulation probe comprising:
      a longilineal body having a central channel void of material running therethrough, extending between a distal portion and a proximal end of the probe, the central channel being open at said proximal end and the distal portion of the body being capable of transmitting a predetermined wavelength;
      electrodes affixed to an outer surface of the body in the distal portion of the probe for electric brain stimulation; and
      electrical terminals affixed to an outer surface of the body in the proximal end of the probe and connected to the electrodes for their electric power supply;
   an electrical housing comprising a channel having electrical terminals housed therein, said channel being open at one of its ends to receive the proximal portion of the probe to place into contact the electrical terminals of the probe and the electrical terminals of the housing; and
   an electrical extension lead affixed to the electrical housing and connected to the electrical terminals of the housing,
   wherein the channel of the electrical housing is open at the other one of its ends;
   and
   wherein the device further comprises:
      a waveguide capable of guiding the predetermined wavelength, housed at least partly in the central channel of the probe body, and extending all the way to the distal portion of the probe for the illumination of the brain therethrough; and
      a transmitter housing capable of being connected to the proximal end of the waveguide for the injection into it of the predetermined wavelength.

2. The deep brain stimulation device of claim 1, wherein the distal portion of the waveguide and the distal portion of the probe have a length in the range from 2 millimeters to 5 millimeters.

3. The deep brain stimulation device of claim 1, wherein the wavelength is in the range from 670 nanometers to 1,070 nanometers, and preferably from 670 to 810 nanometers, and wherein the optical power transmitted by the distal portion of the waveguide is smaller than or equal to 10 milliwatts.

4. The deep brain stimulation device of claim 1, wherein the waveguide is a HCS-type optical fiber having a silica core with a diameter in the range from 125 micrometers to 300 micrometers.

5. An electrical extension lead for a connection with a deep brain stimulation probe, said probe comprising a longilineal body and electrical terminals affixed to an outer surface of a proximal portion of the probe body, said electrical extension lead comprising:
   an electrical housing comprising:
      a channel open at a first and a second ends, the channel being capable of receiving the proximal portion of the body of the probe when the latter is introduced through the first end of the channel;
      electrical terminals housed in the channel of the electrical housing and capable of coming into contact with the probe terminals when the proximal portion thereof is introduced into the channel of the housing through the first end of the channel;
   and an electrical extension lead comprising electrical conductors connected to the electrical terminals of the housing, said electrical extension lead being affixed to the housing without obstructing the second end of the housing channel.

6. A method of testing the optical operation of a first and a second stimulation devices of claim 1, the probes of the two devices being pre-implanted in the brain with their distal portions housed in an area of the brain to be treated, the method comprising:
   injecting a radiation having a predetermined wavelength into the waveguide of the first device through the proximal end of the waveguide and measuring said radiation at the proximal end of the waveguide of the second device;
   injecting a radiation having the same wavelength into the waveguide of the second device through the proximal end of the waveguide and measuring said radiation at the proximal end of the waveguide of the first device; and
   diagnosing the optical operation of the assembly formed by the probes and the waveguides housed therein according to the measurements.

* * * * *